United States Patent [19]
Benedict

[11] 3,988,433
[45] Oct. 26, 1976

[54] ORAL COMPOSITIONS FOR PREVENTING OR REMOVING STAINS FROM TEETH

[75] Inventor: James John Benedict, Cincinnati, Ohio

[73] Assignee: The Procter & Gamble Company, Cincinnati, Ohio

[22] Filed: June 11, 1975

[21] Appl. No.: 586,005

Related U.S. Application Data

[63] Continuation-in-part of Ser. No. 387,560, Aug. 10, 1973, abandoned.

[52] U.S. Cl. .................................... 424/53; 252/99
[51] Int. Cl.$^2$ ............................................ A61K 7/20
[58] Field of Search ........................ 424/53; 252/99

[56] References Cited
UNITED STATES PATENTS

| | | | |
|---|---|---|---|
| 1,754,914 | 4/1930 | Stoddard | 252/99 |
| 1,863,116 | 6/1932 | Heymann | 424/53 |
| 2,090,437 | 8/1937 | Woldman | 424/53 |
| 3,029,188 | 4/1962 | Cyr et al. | 424/49 |
| 3,075,921 | 1/1963 | Brocklehurst et al. | 252/99 |
| 3,243,377 | 3/1966 | Stolar et al. | 252/95 |
| 3,639,285 | 1/1972 | Nielson | 252/100 |

*Primary Examiner*—Shep K. Rose
*Attorney, Agent, or Firm*—Ronald L. Hemingway; Thomas H. O'Flaherty; George W. Allen

[57] ABSTRACT

Oral compositions such as toothpastes, mouthwashes and the like containing specific organic peroxyacids which prevent stain or remove stain rapidly and effectively and processes for preventing or removing stain using said compositions.

8 Claims, No Drawings

ORAL COMPOSITIONS FOR PREVENTING OR REMOVING STAINS FROM TEETH

CROSS-REFERENCE TO RELATED APPLICATION

This is a continuation-in-part of application Ser. No. 387,560, filed Aug. 10, 1973, now abandoned.

BACKGROUND OF THE INVENTION

The field of this invention is oral compositions which term is used herein to designate products which in the ordinary course of usage are retained in the oral cavity for a time and in a manner sufficient to contact essentially all of the dental surfaces, but are not intentionally ingested. Such products include, for example, dentifrices, mouthwashes, prophylaxis pastes, and topical solutions.

The peroxyacids of this invention are known, having been disclosed in, e.g., U.S. Pat. No. 3,075,921, Brockelhurst et al., issued Jan. 29, 1963; "Organic Peroxides," Daniel Swern, Editor, published 1970 by John Wiley & Sons, Inc.; and in U.S. Pat. No. 3,749,674, issued July 31, 1973. Said patents and said book are incorporated herein by reference.

SUMMARY OF THE INVENTION

It has now been discovered that certain specific organic peroxyacids disclosed herein can be used in oral compositions to treat oral cavities, and especially teeth, to minimize the amount of stain on, e.g., the teeth. This stain may be either naturally occurring stain, including the stain caused by coffee, tea, smoking and food, or stain of the type caused by the use of antibacterial agents, especially those described in the application of John William Haefele, Ser. No. 338,464, filed Mar. 6, 1973, for "ORAL COMPOSITIONS FOR PLAQUE, CARIES, AND CALCULUS RETARDATION WITH REDUCED STAINING TENDENCIES", now abandoned. Said application is incorporated herein by reference.

It is surprising that these specific organic peroxyacids are so effective against stain, whereas most other organic peracids, other types of organic percompounds, and inorganic percompounds are relatively ineffective except when used at elevated temperatures and/or for long exposure times.

DETAILED DESCRIPTION OF THE INVENTION

This invention relates to oral compositions effective in reducing the amount of stain on stained teeth comprising an effective amount of a bleaching compound selected from the group consisting of (1) alkyl diperoxyacids containing alkylene groups containing from 5 to 11 carbon atoms including substituted alkyl diperoxyacids, e.g., those containing up to two substituents selected from the group consisting of chloro, fluoro, nitro, trifluoromethyl, trimethylammonium, carboxy, and acetyl groups per methylene group, and (2) aryl peroxyacids having the formula:

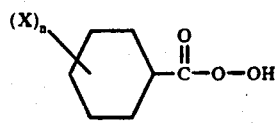

wherein at least one X is a substituent group having a Hammett sigma constant equal to or greater than +0.2, and $n$ is a number from 1 to 3. Groups having Hammett sigma constants greater than +0.2 are strongly electron withdrawing and increase the reactivity of the peroxyacid group. These substituents are placed at either the meta- or para- position. Hammett sigma constants are described in Jaffe, Chemical Reviews, 53, 191 (1953), which is incorporated herein by reference.

Examples of X groups which are preferred include chloro, m-fluoro, nitro, trifluoromethyl, trimethylammonium, cyano, carboxy, percarboxy, and acetyl groups. X may also be an iodo, bromo, amino, or amido group, but such reactive groups are desirably not present since they can react with the peroxy group or groups, thereby reducing the stability and effectiveness of the compound.

In general, the aromatic peroxyacids are preferred since they are more effective. Also preferred in accordance with the teachings of U.S. Pat. No. 3,075,921 are those substituted peroxybenzoic acids having a melting point not lower than 50° C. since they are more stable. In general, those substituted peroxybenzoic acids having substituents with higher positive Hammett sigma constants are preferred. Multiple groups may be present. It is desirable to avoid substituent groups which will react with the peroxygen moiety. Where quaternary groups are present as substituents, it is preferred that the anion be one which is compatible with the peroxygen moiety and which will leave the compound water-soluble or water-dispersible. Suitable anions include fluoride, nitrate, sulfate, and methylsulfate anions. The unsubstituted alkyl diperoxyacids are preferred alkyl diperoxyacids.

The mode of action of these organic peroxyacids is not known. Similar organic peroxygen compounds do not provide stain prevention and/or removal like the specific organic peroxyacids of this invention. It has been noted that the specific peroxygen acids of this invention inhibit the calcification of stain, thereby promoting removal of the stain by mechanical action. The organic peroxyacids of this invention are antibacterial agents. Antibacterial agents inhibit the growth of plaque and contribute to reduction in caries, gingivitis, etc., by controlling the bacterial population in the mouth.

It is, of course, preferred that the substituents be such that the resulting organic peroxyacid is non-toxic, as used. It will be recognized that if the teeth are artificial, they can be removed, treated, and then cleaned so as to avoid exposure to any toxic material.

The process of this invention involves treating the stained teeth with an aqueous oral composition comprising an effective amount of an organic peroxyacid selected from the group consisting of alkyl diperoxyacids containing alkylene groups containing from 5 to 11 carbon atoms including substituted alkyl diperoxyacids, e.g., those containing up to two substituents selected from the group consisting of halogen atoms and nitro, trifluoromethyl, trimethylammonium, carboxy, and acetyl groups per methylene group, and aryl peroxyacids having the formula:

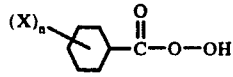

wherein at least one X is a substituent group having a Hammett sigma constant equal to or greater than +0.2, and $n$ is a number from 1 to 3.

COMPOSITIONS

The compositions of this invention preferably contain from about 2% to about 50%, preferably from about 5% to about 35%, of the organic peroxyacid of this invention when they are concentrates and from about 0.01% to about 5%, preferably from about 0.05% to about 0.5%, of the organic peroxyacid of this invention when the compositions are used to treat the stained teeth.

THE CONCENTRATES

These concentrates can be either aqueous or anhydrous. If they are to be stored for any appreciable amount of time and if there is any reactive material present, anhydrous products are often preferred. The compositions of this invention can include the usual components of toothpastes, toothpowders, mouthwashes, prophylaxis pastes, and the like as more fully described hereinafter, but normally will be limited to materials which do not contain reactive sites such as amino, amido, hydroxy, iodo, bromo, and sulfhydryl groups and unsaturated, imino, and thioether linkages when the product is to be stored for any appreciable period of time. It is contemplated, however, that compositions containing such reactive ingredients can be prepared when they are to be used immediately, e.g., when the user prepares them by coextruding two separate compositions. A mouthwash concentrate is a preferred embodiment of this invention since, unlike toothpastes, there are less components present which can react with the peroxyacid. Toothpaste compositions conventionally contain abrasive materials, sudsing agents, binders, humectants, flavoring and sweetening agents. Most of these ingredients cannot be stored with the oxidizing agents. Therefore, toothpastes according to this invention will normally be two component compositions in separate containers or chambers, to be combined just before use.

Abrasives normally are added only to dilute compositions intended for immediate use since many abrasives tend to make the peroxyacids unstable. Abrasives include dicalcium orthophosphate, calcium carbonate, beta-phase calcium pyrophosphate, prepared, for example, in accordance with the teachings of Schweizer, U.S. Pat. No. 3,112,247, granted Nov. 26, 1963, particulate thermosetting polymerized resins, e.g., as described by Cooley et al. in U.S. Pat. No. 3,070,510, granted Dec. 25, 1962 (e.g., melamines, phenolics, ureas, melamine-ureas, melamine formaldehydes, urea formaldehydes, melamine-urea formaldehydes, cross-linked epoxides and cross-linked polyesters), alumina, silica xerogels of the type disclosed in the abandoned application of Briner et al., Ser. No. 329,782, filed Feb. 9, 1973, and other phosphate and silica abrasives such as insoluble sodium metaphosphate. Mixtures of abrasives can also be used. The total amount of abrasive in the dentifrice embodiments of this invention can range from 0.5% to 95% by weight of the dentifrice. Preferably, toothpastes contain from about 20% to about 60% by weight of abrasive. Abrasive particle size preferably ranges from about 1 micron to about 30 microns.

Suitable sudsing agents are those which are reasonably stable and form foam throughout a wide pH range, preferably nonsoap anionic organic synthetic detergents which are relatively unreactive with the peroxyacids of this invention. Examples of such agents are water-soluble salts of alkyl sulfate having from 10 to 18 carbon atoms in the alkyl radical, such as sodium lauryl sulfate. Other somewhat more reactive detergents include water-soluble salts of sulfonated monoglycerides of fatty acids having from 10 to 18 carbon atoms, such as sodium monoglyceride sulfonates; salts of $C_{10}$–$C_{18}$ fatty acid amides of taurine, such as sodium N-methyl-N-palmitoyl tauride; salts of $C_{10}$–$C_{18}$ fatty acid esters of isethionic acid; and substantially saturated aliphatic acyl amides of saturated monoaminocarboxylic acids having 2 to 6 carbon atoms and in which the acyl radical contains 12 to 16 carbon atoms, such as sodium N-lauroyl sarcoside. Mixtures of two or more sudsing agents can be used. Other suitable sudsing agents include the nonionic, cationic, zwitterionic and amphoteric nonsoap organic synthetic detergents.

The nonionic synthetic detergents which can be used with the oral compositions of the present invention should not be part of concentrated compositions which are to be stored for long periods of time which contain the peroxyacids when the nonionic detergents contain reactive hydroxyl groups. Nonionic synthetic detergents may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water insolubility, has a molecular weight of from about 900 to about 5,000. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Other suitable nonionic synthetic detergents include:
1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.
2. Those derived from the condensation of ethylene oxide with the product resulting from the reaction of propylene oxide and ethylene diamine — products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

The following amine oxide and phosphine oxide nonionic synthetic detergents, when they do not contain hydroxyl groups, are compatible with the peroxyacids.

4. Long chain tertiary amine oxides corresponding to the following general formula, $R_1R_2R_3N \rightarrow O$, wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semi-polar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula $RR'R''P \rightarrow O$, wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)-phosphine oxide,
stearyldimethylphosphine oxide,
cetylethylpropylphosphine oxide,
oleyldiethylphosphine oxide,
dodecyldiethylphhosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:
octadecyl methyl sulfoxide, 2-ketotridecyl methyl sulfoxide,
3,6,9-trioxaoctadecyl 2-hydroxyethyl sulfoxide,
dodecyl methyl sulfoxide,
oleyl 3-hydroxy propyl sulfoxide,
tetradecyl methyl sulfoxide,
3-methoxytridecyl methyl sulfoxide
3-hydroxytridecyl methyl sulfoxide,
3-hydroxy-4-dodecoxybutyl methyl sulfoxide.

The zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. When these detergents do not contain hydroxyl groups, they are usually compatible with the peroxyacids. A general formula for these compounds is:

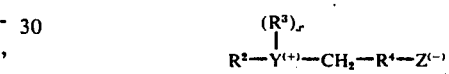

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom, $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradecoxylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxy-propane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]2-hydroxypentane-1-sulfate.

The cationic synthetic detergents useful in the oral compositions of the present invention can be broadly defined as quaternary ammonium compounds having 1 long alkyl chain containing from about 8 to about 18 carbon atoms such as lauryl trimethylammonium chloride; cetyl pyridinium chloride; cetyl trimethylammonium bromide; di-isobutyphenoxyethoxyethyldimethylbenzylammonium chloride; coconutalkyltrimethylammonium nitrite; cetyl pyridinium fluoride; etc. Especially preferred are the quaternary ammonium florides described in U.S. Pat. No. 3,535,421 incorporated by reference hereinbefore, where said quaternary ammonium fluorides have detergent properties. Cationic detergents free of hydroxyl and reactive nitrogen groups and linkages are normally compatible with the peroxyacids.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, dodecyl-$\beta$-alanine, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The sudsing agent can be present in the dentifrice compositions of this invention in an amount from 0.5% to 10%, preferably from 1% to 5%, by weight of the total compositions.

One can also include a water-soluble fluoride compound in the compositions of this invention in an amount to give a fluoride concentration of from about 0.0025% to about 5%, preferably from about 0.005% to about 2.0%, to provide additional anticaries effectivenss. Suitable fluoride sources are disclosed in the EXAMPLES. Preferred fluorides are sodium, indium, and stannous fluorides, and sodium monofluorophosphate. Suitable fluorides are disclosed in U.S. Pat. No. 3,535,421, which is incorporated herein by reference.

All parts, percentages and ratios herein are by weight unless otherwise indicated.

In preparing toothpastes, it is necessary to add some thickening material to provide a desirable consistency. However, almost all thickening agents, except polymeric polyester compounds, e.g., polyethylene or polypropylene oxide (M.W. 300 to 1,000,000), capped with alkyl or acyl groups containing 1 to about 18 carbon atoms will react with the peroxyacids. When the peroxyacids are formulated separately, preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition. Alternatively, the composition can contain up to about 36% of a paraffin oil.

Suitable flavoring agents include oil of wintergreen, oil of peppermint, oil of spearmint, oil of sassafras, and oil of clove. Sweetening agents which can be used include saccharin, dextrose, levulose and sodium cyclamate.

In a preferred embodiment, because of its reactivity, the organic peroxyacid will be formulated into a composition consisting essentially of an inert organic or inorganic diluent selected for its limited reactivity with the oxidizing material. The primary function of the inert material is to support the peroxyacid and other desired adjuncts in the proper concentrations, either in a single composition which can be added to water to form a composition for treating the oral cavity or as part of a two-component composition, one of which may be aqueous in nature, and the other of which is anhydrous in nature. These two compositions can be mixed to form the treatment composition.

The organic diluent can be either a liquid or a soft wax, preferably a liquid. As used herein, "saturated" is intended to include compounds containing aryl as well as saturated alkyl moieties. "Polyoxyalkylene" as used herein includes ethoxylated and propoxylated materials.

The organic diluent can desirably be a saturated nonionic synthetic detergent of the ethoxylated nonionic type capped with an alkyl or acyl group to eliminate the reactive hydroxy group. Nonionic synthetic detergents can be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Another class has semipolar characteristics. Preferred classes of nonionic synthetic detergents are as follows:

1. A class of nonionic synthetic detergents under the tradename of "Pluronic". These compounds are formed by condensing ethylene oxide with a hydrophobic base formed by the condensation of propylene oxide with propylene glycol which is then "capped" by alkylating ($C_1$–$C_{18}$) or acylating ($C_2$–$C_{18}$) the molecule to form ether or ester groups. The hydrophobic portion of the molecule which, of course, exhibits water insolubility, has a molecular weight of from about 900 to 5,000. The addition of polyoxyethylene radicals to this hydrophobic portion tends to increase the water solubility of the molecule as a whole and the liquid character of the product is retained up to the point where the polyoxyethylene content is about 50 percent of the total weight of the condensation product.

2. The polyethylene oxide condensates of alkyl phenols, e.g., the condensation products of alkyl phenols having an alkyl group containing from about 6 to 12 carbon atoms in either a straight-chain or branched-chain configuration with ethylene oxide, the said ethylene oxide being present in amounts equal to 5 to 25 moles of ethylene oxide per mole of alkyl phenol. The condensates are "capped" as with group 1. The alkyl substituent in such compounds may be derived from polymerized propylene, diisobutylene, octene, or nonene, for example.

3. Those nonionic synthetic detergents derived from the condensation of ethylene oxide with the product resulting from the reaction of propylene oxide and ethylene diamine. The condensates are "capped" as in group 1. For example, compounds containing from about 40 percent to about 80 percent polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000 are satisfactory.

4. The condensation product of aliphatic alcohols having from 8 to 22 carbon atoms, in either straight-chain or branched-chain configuration, with ethylene oxide, e.g., a coconut alcohol ethylene oxide condensate having from 5 to 40 moles of ethylene oxide per mole of coconut alcohol, the coconut alcohol fraction having from 10 to 14 carbon atoms.

Other preferred organic diluents include saturated fatty acids containing from 8 to 22 carbon atoms such as coconut fatty acid, lauric acid, cetic acid (also called cetylic), and stearic acid, saturated acylate esters containing from about 10 to 80 carbon atoms wherein the fatty acyl group contains from 2 to about 18 carbon atoms and from 1 to about 3 carboxyl groups, and the alcohol group contains from 1 to about 18 carbon atoms and from 1 to about 6 hydroxy groups, e.g., methyl laurate, ethylene glycol dilaurate, dibutyl adipate, propylene glycol dimyristate and tristearin, mineral oil having a viscosity at 75° F. of from about 50 to about 700 Saybolt Seconds Furol (SSF), and saturated aliphatic hydrocarbons containing from about 10 to about 20 carbon atoms such as decane, 2-ethyldecane, tetradecane, isotetradecane, hexadecane and eicosane, as well as mixtures of said hydrocarbons.

Especially preferred organic diluents include mineral oil, saturated aliphatic hydrocarbons, diesters of propylene glycol and triesters of glycerine.

In an especially preferred embodiment of the invention a thickened form of the mineral oil or aliphatic hydrocarbon is used as the organic diluent, the thickening agent being selected from a group of specific types of organic waxes. These thickening agents have excellent compatibility with the peroxyacids and, when used in proper proportions with the mineral oil or hydrocarbons are effective in producing a composition which has a viscosity within the range of normal toothpaste compositions, i.e., a Brookfield viscosity at 75° F. of from about 15 to about 100. Such composition can be spread from a squeezable tube onto a toothbrush and brushed upon the teeth in the conventional manner of toothpaste usage. The thickening agents are selected from the group consisting of:

1. saturated fatty acid triglycerides having melting points of from about 130° to about 250° F.

2. microcrystalline waxes having a melting point of from about 130° to about 250° F. and a penetration value of from about 0.5 to about 20 as determined by ASTM Test D-1321 and 3. polyethylene waxes having a melting point of from about 130° to about 250° F. and a penetration value at 77° F. of from about 0.5 to about 20 as determined by ASTM Test D-1321.

The amount of any particular thickening agent in these compositions is selected so as to produce the desired Brookfield viscosity. Generally a level of thickening agent within the range of from about 5% to about 30% by weight of the composition is used. Thus, these especially preferred compositions consist essentially of from about 2% to about 50% of the peroxyacid (preferably from about 5% to 35%), from about 5% to about 30% of a thickening agent selected from the types of enumerated above, and the balance mineral oil or saturated aliphatic hydrocarbon, the specific amount of thickening agent being chosen so as to produce a Brookfield viscosity at 75° F. of from about 15 to about 100. The Brookfield viscosities quoted herein are determined on a Brookfield RVT ½ Heliopath Viscometer using an E spindle set at 2.5 rpm rotational speed.

Examples of Type 1 thickening agents are triglycerides such as myristic acid triglyceride, stearic acid triglyceride, and palmitic acid triglyceride. Mixtures of saturated fatty acid triglycerides such as those which make up hydrogenated tallow, hydrogenated soybean oil and hydrogenated cottonseed oil are also suitable.

Examples of Type 2 thickening agents are White Micro Wax (melting point 163°–169° F., penetration value 9) sold by International Wax Refining Company, Petrolite C-1035 (melting point 197°–202° F., penetration 4–5), Be Square 195 (melting point 193°–198° F., penetration 6–7), Ceramer 67 (melting point 200°–215° F., penetration 2.5–3.5) and Petrolite C-8500 (melting point 200°–210° F., penetration 4–7), all sold by Bareco Division of Petrolite Corporation.

Examples of Type 3 thickening agents are Polywax 655 (melting point 215° F, penetration 3.0), Polywax 500 (melting point 185° F., penetration 5.0) and Polywax E2020 (melting point 242° F., penetration 1.0), all sold by Bareco Division of Petrolite Corporation.

Inorganic diluents which can be present in the compositions of the invention include alkaline earth and alkali metal sulfates. Such diluents are especially desirable with diperisophthalic acid, which can be hazardous without some such diluent. Normally, diperisophthalic acid is sold in commerce in the form of granular dilute compositions, wherein the diluent is an alkali metal or alkaline earth metal salt, especially the sulfate salt. Thus, it is to be understood that the compositions disclosed and claimed herein can include such inorganic diluents which customarily accompany the peroxyacids.

Desirable flavor ingredients which can be included in the concentrates are "saturated" esters such as ethyl butyrate, menthyl acetate, and benzyl acetate; saturated ketones such as methyl amyl ketone, menthone, and eucalyptol.

Several representative oral compositions illustrating this invention are set forth in the following examples.

EXAMPLE I

Aqueous compositions containing about 0.3% by weight of the following indicated organic peroxyacids were prepared and used to treat naturally stained tooth surfaces with indicated results: m-chloroperoxybenzoic acid — excellent stain removal; diperisophthalic acid — very good stain removal; diperoxyadipic acid — good stain removal; diperazelaic acid — good stain removal; dipersebacic acid — fair stain removal; p-nitroperoxybenzoic acid — excellent stain removal;

and m-trifluoromethylperoxybenzoic acid — very good stain removal.

EXAMPLE II

The following peroxyacid concentrates are used alone and with the dentifrice and mouthwash and compositions disclosed in two abandoned U.S. patent applications of Haefele, Ser. No. 338,472, filed Mar. 6, 1973 and Ser. No. 338,464, filed Mar. 6, 1973, to prepare dilute aqueous oral treatment compositions by diluting with water to give a concentration of from 0.2% to 0.6%. The treatment compositions are then applied to stained teeth to remove stain and prevent its formation.

| (A) | Percent |
|---|---|
| p-chloroperoxybenzoic acid | 6 |
| Triacetin | balance |
| (B) | |
| m-chloroperbenzoic acid | 8 |
| Mineral oil (SSF-60) | balance |
| (C) | |
| Diperisophthalic acid | 10 |
| Menthyl acetate and methone (1:1) | 2 |
| Sodium alkyl (C$_{14}$-C$_{12}$) sulfate | 4 |
| Diethylether of polyethylene glycol (M.W. 1000) | balance |
| (D) | |
| Diperoxyadipic acid | 9 |
| Potassium polyethoxylated (4) coconut fatty alcohol sulfate | 2 |
| Methyl laurate | balance |
| (E) | |
| Diperazelaic acid | 8 |
| Dimethyldodecylphosphine oxide | 1 |
| Diacetyl polyethylene oxide (M.W. 800) | balance |
| (F) | |
| Dipersebacic acid | 12 |
| Sodium coconut alkyl sulfate | 2 |
| Coconut alkyldimethylamine oxide | 2 |
| Magnesium sulfate | 23 |
| Sodium sulfate | balance |
| (G) | |
| p-nitroperoxybenzoic acid | 4 |
| M-trifluoromethylperoxybenzoic acid | 2 |
| Coconut alkylbenzyldimethylammonium chloride | 1 |
| Ethyl butyrate, benzyl acetate, methyl amyl ketone and eucalyptol (1:2:1:3) | 4 |
| Triacetin | 45 |
| Diethyl ether of polyethylene oxide (M.W. 1200) | 40 |
| Methyl butyl ether | balance |
| (H) | |
| M-trifluoromethyl; P-nitroperoxybenzoic acid | 3 |
| Cetyl pyridinium sulfate | 1.5 |
| Saccharin | 0.9 |
| Anethole | 0.6 |
| Methyl salicylate | 0.6 |
| Methyl laurate | 10 |
| Triacetin | balance |
| (I) | |
| P-(trimethylammonium sulfate) peroxybenzoic acid | 4 |
| Calcium sulfate | balance |
| (J) | |
| m-chloroperoxybenzoic acid | 5 |
| Barium sulfate | balance |

EXAMPLE III

Dentures were soaked overnight in an aqueous solution containing 0.2% 1,6-di(N-p-chlorophenyldiguanido) hexane digluconate (chlorhexidine) and worn during the day until a brown stain was formed. These dentures were treated with 0.2% diperisophthalic acid and 0.2% diperadipic acid aqueous solutions buffered to a pH of about 7.5 with phosphate buffer for a period of three minutes at ambient temperatures. The brown color was essentially all gone after this treatment.

EXAMPLE IV

Stain was formed by dipping porous porcelain plates alternately in chlorhexidine containing solution and in a coffee solution until a brown stain developed. These plates were then treated with 0.2% aqueous solutions of the following peroxyacids with the indicated results: m-chloroperoxybenzoic acid — excellent; diperisophthalic acid — excellent; diperadipic acid — very good.

EXAMPLE V

A concentrate of the present invention was prepared according to the following formula:

| | Parts by weight |
|---|---|
| White mineral oil USP | 61.5 |
| Polywax 655 * | 10.7 |
| Suprox FD ** | 27.8 |
| | 100.0 |

* Polyethylene wax, melting point 215° F., penetration 3.0.
** Dry mixture consisting of 25% diperisophthalic acid, 50% magnesium sulfate and 25% water, from PPG Industries.

The Polywax was added to the mineral oil with stirring at 200° F., causing the Polywax to dissolve in the oil. The mixture was rapidly cooled to 100° F. and the Suprox FD was then mixed in to form a homogeneous mixture having a Brookfield viscosity at 75° F. of 30.

EXAMPLE VI

A concentrate of the present invention was prepared according to the following formula:

| | Parts by weight |
|---|---|
| White mineral Oil USP | 82.0 |
| Hydrogenated cottonseed oil | 8.0 |
| Suprox * | 10.0 |
| | 100.0 |

* Dry mixture diperisophthalic acid and 70% MgSO$_4$ . 7H$_2$O from PPG Industries.

The oil was heated to 158° F. and the hydrogenated cottonseed oil was mixed in and allowed to dissolve in the oil. The mixture was then cooled to room temperature. The Suprox was then added with mixing to form a homogeneous mixture, which was then passed once through a dentifrice colloid mill with a gap setting of 0.030 in.

EXAMPLE VII

A concentrate of the present invention was prepared according to the following formula:

| | Parts by weight |
|---|---|
| Hexadecane | 56.0 |
| Polywax 500 * | 19.0 |
| Suprox ** | 25.0 |
| | 100.0 |

* Polyethylene wax, melting point 185° F. penetration value 5.0.
** See Example V.

The hexadecane was heated to 190° F. and the wax was mixed in and allowed to dissolve in the oil. The mixture was then rapidly cooled to room temperature. The Suprox FD was then added and the entire composition was mixed with high shear in a Waring blender.

The resulting composition was a homogeneous composition with a Brookfield viscosity at 75° F. of 28.

The above concentrations can also be mixed in ratios of from about 3:1 to about 8:1 with conventional mouthwashes and toothpastes to provide an intermediate concentrate which can be diluted with water in a 1:1 to 1:3 ratio to provide an aqueous oral treatment composition which when applied to tooth surfaces removes and/or prevents stain.

What is claimed is:

1. A tooth-stain bleaching composition in concentrate form consisting essentially of:
   I. from about 2% to about 50% of a bleaching compound selected from the group consisting of:
   aryl peroxyacids having the formula:

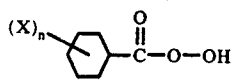

wherein at least one X is a substituent group having a Hammett sigma constant equal to or greater than +0.2, and n is a number from 1 to 3, said substituents being either in the meta or para portion; and
   II. the balance an inert organic diluent which is an organic liquid or soft wax selected from the group consisting of:
   A. saturated fatty acids containing from about 8 to about 22 carbon atoms; and
   B. saturated acylate esters containing from about 10 to about 80 carbon atoms wherein the acyl group contains from about 2 to about 22 carbon atoms and from 1 to about 3 carboxyl groups, and the alcohol group contains from 1 to about 18 carbon atoms and from 1 to about 6 hydroxy groups.

2. The composition of claim 1 wherein the X substituents on the aryl peroxyacid are selected from the groups consisting of chloro, m-fluoro, nitro, trifluoromethyl, trimethylammonium, cyano, carboxy, percarboxy and acetyl groups.

3. The composition of claim 2 wherein the aryl peroxyacid is diperisophthalic acid.

4. A composition according to claim 3 containing from about 5% to about 35% of the diperisophthalic acid.

5. The method of removing stain from teeth in the mouth or in dentures with a composition of claim 1, comprising the steps of diluting said composition to a concentration of aryl peroxyacid of from about 0.01% to about 5% and contacting the stained teeth with the diluted composition.

6. The method of claim 5 wherein the composition is diluted to a concentration of from about 0.05% to about 0.5% of the aryl peroxacid.

7. The method of claim 6 wherein the aryl peroxyacid is perisophthalic acid.

8. The method of claim 7 wherein the stain on the teeth has been formed by the application of salts of 1, 6-di (N-p-chlorophenyldiguanido)hexane, or related bis-biguanide compounds.

* * * * *